United States Patent
Kawai

(10) Patent No.: US 9,867,158 B2
(45) Date of Patent: Jan. 9, 2018

(54) MOBILE INFORMATION TERMINAL, CONTROL METHOD THEREOF, AND STORAGE MEDIUM

(71) Applicant: CANON KABUSHIKI KAISHA, Tokyo (JP)

(72) Inventor: Takatomo Kawai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/222,408

(22) Filed: Mar. 21, 2014

(65) Prior Publication Data

US 2014/0287775 A1 Sep. 25, 2014

(30) Foreign Application Priority Data

Mar. 25, 2013 (JP) ................. 2013-062499

(51) Int. Cl.
  *H04W 24/00* (2009.01)
  *H04W 64/00* (2009.01)
  *H04W 4/02* (2009.01)
  *H04L 29/08* (2006.01)

(52) U.S. Cl.
  CPC .............. *H04W 64/00* (2013.01); *H04L 67/12* (2013.01); *H04W 4/023* (2013.01)

(58) Field of Classification Search
  CPC ........ H04W 4/02; H04W 64/00; H04W 4/021; H04W 4/025; H04W 4/04; H04W 4/008; H04W 64/003; H04W 40/20; H04W 48/04; H04W 4/027; H04W 4/023; H04W 4/028; H04L 67/34; H04L 67/22; H04L 2209/88; H04L 63/123; H04L 67/141; G06F 2221/2111

USPC ...................................................... 455/456.1
See application file for complete search history.

(56) References Cited

U.S. PATENT DOCUMENTS

| | | | |
|---|---|---|---|
| 2004/0054263 A1* | 3/2004 | Moerman et al. ............ 600/300 |
| 2005/0021369 A1* | 1/2005 | Cohen et al. ..................... 705/2 |
| 2006/0138224 A1* | 6/2006 | Azami ................. G06Q 20/346 235/385 |
| 2011/0093278 A1* | 4/2011 | Hutton ................... G06Q 10/00 705/2 |
| 2012/0259658 A1* | 10/2012 | Matz ................................ 705/3 |
| 2013/0031598 A1* | 1/2013 | Whelan et al. .................. 726/1 |

FOREIGN PATENT DOCUMENTS

| | | |
|---|---|---|
| JP | 2005-071071 A | 3/2005 |
| JP | 2005-293034 A | 10/2005 |
| JP | 2011-136054 A | 7/2011 |
| JP | 2012-248027 A | 12/2012 |
| WO | 2006/115048 A1 | 11/2006 |
| WO | 2011/114617 A1 | 9/2011 |

\* cited by examiner

*Primary Examiner* — Kwasi Karikari
(74) *Attorney, Agent, or Firm* — Canon USA Inc., IP Division

(57) ABSTRACT

A mobile information terminal includes a setting unit configured to store position information for browsing patient information. The mobile information terminal downloads the patient information from a server via a communication unit to store the patient information in a data storage unit according to a result of comparing position information specified by a terminal position specifying unit with the position information stored by the setting unit.

11 Claims, 13 Drawing Sheets

FIG. 2

| PATIENT ID | BROWSABLE POSITION INFORMATION |
|---|---|
| 00123 | E139:46:27, N35:40:23 |
| 10001 | E139:46:30, N35:41:25 |
| 23456 | E139:45:15, N35:29:20 |

FIG. 12

| PATIENT ID | BROWSABLE POSITION INFORMATION | MEDICAL TREATMENT TYPE INFORMATION |
|---|---|---|
| 00123 | E139:46:27,N35:40:23 | CONTINUED |
| 10001 | E139:46:30,N35:41:25 | NEW |
| 23456 | E139:45:15,N35:29:20 | CONTINUED |

MOBILE INFORMATION TERMINAL, CONTROL METHOD THEREOF, AND STORAGE MEDIUM

BACKGROUND

1. Field

Aspects of the present invention generally relate to a mobile information terminal for browsing, for example, patient information, a control method thereof, a storage medium, and an information security technique when the patient information is browsed outside of a hospital.

2. Description of the Related Art

In a medical field, such as a hospital, computerization of a medical record recording a patient's condition or a treatment process has progressed, and uniform management and sharing of patient information have been achieved.

The patient information in the computerized medical record can be copied to a mobile information terminal to be taken out, and is used for browsing the patient information at the patient's home when making a house visit.

On the other hand, the computerized medical record can be processed by a computer, and a risk of information leakage and alteration due to copying or exchanging in a network is higher than in the case of using a paper medical record. The patient information in a medical record needed by a doctor for medical examination includes highly confidential personal information on a disease condition or the like. Thus, with the computerization of the medical record, stronger protection of the patient information is necessary.

Japanese Patent Application Laid-Open No. 2011-136054 discusses a method for limiting taking out of the computerized patient information to the outside of the hospital where security is low. According to this method, permission information for transferring medical information to a mobile information terminal is set, and only permitted information can be transferred to the mobile information terminal, thereby suppressing careless taking-out.

According to the technique discussed in Japanese Patent Application Laid-Open No. 2011-136054, the risk of information leakage is reduced by limiting transferrable information at a transfer stage to the mobile information terminal.

However, no consideration is given to information security after the transfer of information to the mobile information terminal. When patient information is transferred to the mobile information terminal at the hospital, and then the mobile information terminal is brought out for a house visit, it is difficult to prevent leakage of the patient information caused by a terminal user's mistake, such as a loss of the terminal or peeping, on the way of the house visit.

SUMMARY

Aspects of the present invention are generally directed to a technique for preventing leakage of patient information caused by a terminal user's mistake on the way of, for example, moving to a visiting destination.

According to an aspect of the present invention, a mobile information terminal includes a position specifying unit configured to specify a position of the mobile information terminal, a communication unit configured to communicate with an external device that manages personal information, a storage unit configured to store position information set for each piece of personal information for browsing the personal information, and a download control unit configured to download the personal information from the external device via the communication unit according to a result of comparing the position information specified by the position specifying unit with the position information stored by the storage unit.

Further features and aspects of the present disclosure will become apparent from the following detailed description of exemplary embodiments with reference to the attached drawings.

BRIEF DESCRIPTION OF THE DRAWINGS

FIG. 2 is a table indicating an example of position information.

FIG. 12 is a table indicating an example of a position/medical treatment type information.

DESCRIPTION OF THE EMBODIMENTS

Various exemplary embodiments will be described in detail below with reference to the drawings.

Figure 1:
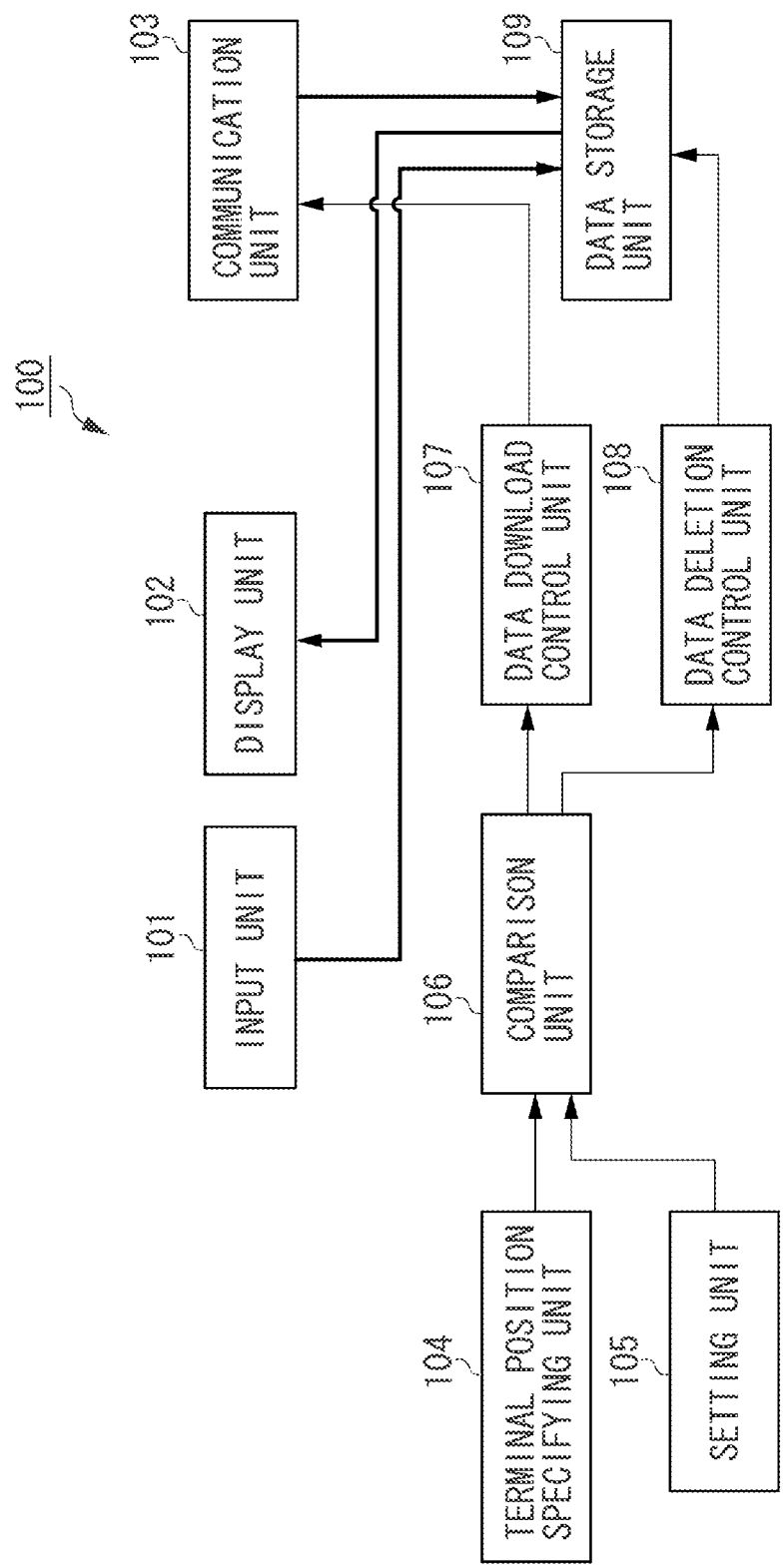
FIG. 1 is a block diagram illustrating an example of a configuration of a mobile information terminal according to a first exemplary embodiment.

FIG. 1 is a block diagram illustrating a configuration of a mobile information terminal 100 according to a first exemplary embodiment.

An input unit 101, which includes a touch panel and buttons, receives inputs of various operations from a user of the mobile information terminal 100.

A display unit 102, which is a display device, such as a liquid crystal display, displays patient information.

A communication unit 103, which has a communication function for the mobile information terminal 100 to communicate with an external device, performs communication to download patient information from, for example, a server of a hospital.

A terminal position specifying unit 104 specifies a position of the mobile information terminal 100. More specifically, the terminal position specifying unit 104 specifies the position of the mobile information terminal 100 by using a global positioning system (GPS) that is a positioning technology of a current location using an artificial satellite.

A setting unit 105 sets position information (hereinafter, may also be referred to as browsable position information) for browsing the patient information for each piece of patient information (in other words, for each patient) that is personal information. To limit browsable positions for browsing information of a patient to be visited, the setting unit 105 sets the browsable position information in association with a patient ID of the patient. Examples of the browsable positions for the patient information include a patient home, a hospital, and a doctor's home. The browsable position information set at the setting unit 105 is stored in a position information table and stored by the setting unit 105. The position information table is described below.

A comparison unit 106 compares position information (hereinafter, may also be referred to as terminal position information) of the mobile information terminal 100 by the terminal position specifying unit 104 with the browsable position information stored in the position information table. Then, the comparison unit 106 outputs position difference information indicating a difference between both pieces of position information.

A data download control unit 107 controls downloading of the patient information to the mobile information terminal 100. The data download control unit 107 determines whether to permit downloading of the patient information according to the position difference information by the comparison unit 106. When the downloading is permitted, the patient information is downloaded via the communication unit 103 to be stored in a data storage unit 109.

A data deletion control unit 108 controls deletion of the patient information stored in the data storage unit 109. The data deletion control unit 108 determines whether to delete the patient information according to the position difference information by the comparison unit 106. When the deletion is necessary, the patient information stored in the data storage unit 109 is deleted.

The data storage unit 109 stores the patient information. The data storage unit 109 stores the patient information downloaded via the communication unit 103, and the stored patient information is deleted according to an instruction by the data deletion control unit 108. The patient information stored in the data storage unit 109 is displayed on the display unit 102 as necessary. A content of the patient information can be changed according to an instruction from the input unit 101, and the changed patient information is stored.

FIG. 2 illustrates an example of a position information table. The position information table stores a patient identification (ID) 201 and browsable position information 202 set by the setting unit 105.

The patient ID 201 is for identifying a patient, and a unique ID is allocated for each patient. Since the patient ID 201 is also used in a conventional electronic medical record, which may be used.

The browsable position information 202 is information of a position at which patient information of the patient identified by the patient ID 201 is browsable. Each row indicates position information for browsing patient information of each patient. The table illustrated in FIG. 2 indicates that the patient information having a patient ID of 00123 can be browsed at a position of E 139:46:27 (east longitude) and N 35:40:23 (north latitude).

Figure 3:
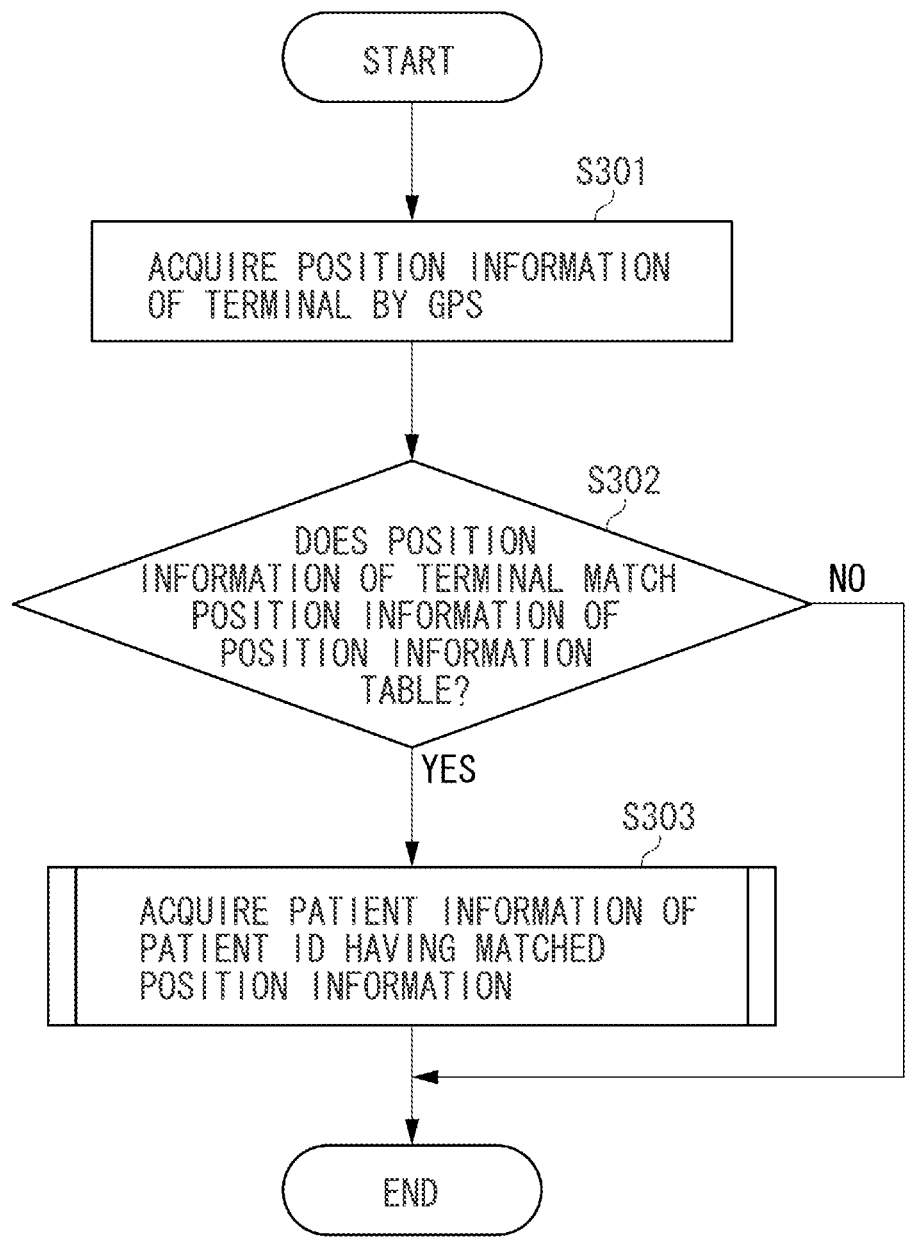
FIG. 3 is a flowchart illustrating an example of a processing procedure when the mobile information terminal according to the first exemplary embodiment obtains patient information.

FIG. 3 is a flowchart illustrating a processing procedure when the mobile information terminal 100 obtains the patient information.

In step S301, the terminal position specifying unit 104 obtains current terminal position information by using the GPS function.

In step S302, the comparison unit 106 compares the terminal position information obtained in step S301 with the browsable position information 202 indicated in the position information table. If there is no patient ID having matched position information (No in step S302), the processing is ended. If there is patient ID having matched position information (YES in step S302), the processing proceeds to step S303. "Having matched position information" may be a condition that a difference in position is within a predetermined range.

In step S303, the data download control unit 107 downloads the patient information of the patient ID having matched position information determined in step S302 via the communication unit 103, and stores the patient information in the data storage unit 109. This data downloading procedure is described below.

The processing procedure may be started in response to a start of a medical record display application at the mobile information terminal 100 at a visiting destination. The terminal position information from the GPS is compared with the browsable position information indicated in the position information table, and when the pieces of the position information match each other, the patient information of the patient ID is downloaded. Alternatively, a position of the mobile information terminal 100 may be always monitored and, when the mobile information terminal 100 enters within a predetermined distance from a visiting destination position registered as the browsable position information, the mobile information terminal 100 may automatically download the patient information.

Figure 4:
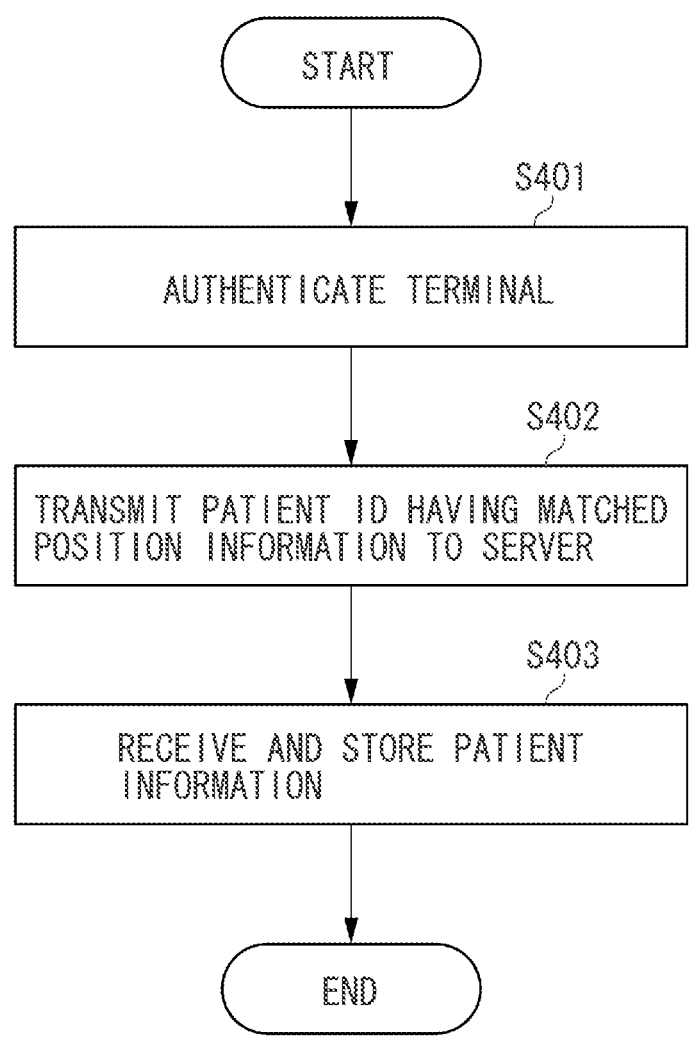
FIG. 4 is a flowchart illustrating an example of a processing procedure when the patient information is downloaded.

FIG. 4 is a flowchart illustrating a processing procedure when the patient information is downloaded in step S303.

In step S401, the data download control unit 107 performs terminal authentication processing between the mobile information terminal 100 and a server that stores and manages the patient information via the communication unit 103. This step is processing for invalidating access from an unidentified terminal to the server. The terminal is authenticated by using an existing authentication technique.

In step S402, the data download control unit 107 transmits the patient ID having matched position information to the server via the communication unit 103. The patient ID of a row where current terminal position information matches the browsable position information 202, which is indicated in the position information table, is transmitted to the server. In step S403, the data download control unit 107 receives the patient information transmitted from the server via the communication unit 103 to store it in the data storage unit 109.

Figure 5:
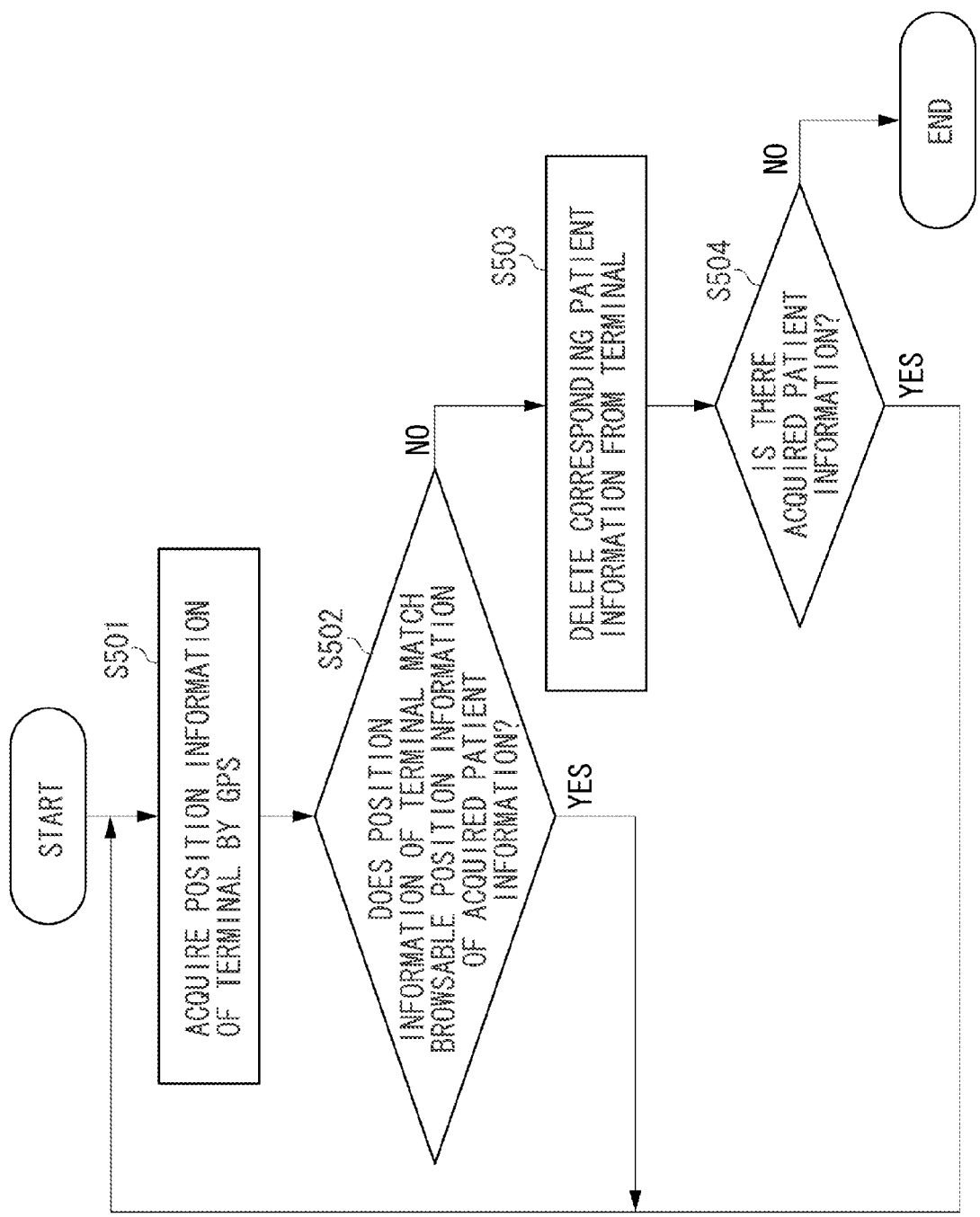
FIG. 5 is a flowchart illustrating an example of a processing procedure when the mobile information terminal according to the first exemplary embodiment deletes the patient information.

FIG. 5 is a flowchart illustrating a processing procedure when the mobile information terminal 100 deletes the patient information.

In step S501, the terminal position specifying unit 104 obtains current terminal position information by using the GPS function.

In step S502, the comparison unit 106 compares the terminal position information obtained in step S501 with the browsable position information associated with the patient ID, of which patient information is stored in the data storage unit 109, in the position information table. If the pieces of the position information match each other (YES in step S502), the processing returns to step S501. If the pieces of the position information do not match each other (NO in step S502), the processing proceeds to step S503. "The pieces of position information match each other" may be a condition that a difference in position is within a predetermined range.

In step S503, the data deletion control unit 108 deletes the patient information of the patient ID having position information, which is determined to be unmatched with the terminal position information in step S502, from the data storage unit 109.

In step S504, the data deletion control unit 108 determines whether there is any obtained patient information in the data storage unit 109. If there is obtained patient information (YES in step S504), the processing returns to step S501. If not (No in step S504), the processing is ended.

The mobile information terminal 100, which has obtained the patient information through the processing procedure illustrated in FIG. 3, deletes the patient information through the processing procedure illustrated in FIG. 5, and continues the processing until there is no more patient information stored in the mobile information terminal 100.

Through the series of procedures illustrated in FIGS. 3 and 5, the mobile information terminal 100 can download the patient information only at a specific position, which has been set in the position information table, associated with the patient. If the position of the mobile information terminal 100 does not match the specific position, which has been set in the position information table, associated with the patient, the patient information is deleted from the mobile information terminal 100.

If the browsable position information 202 is set at a patient home as a visiting destination, a terminal user, such as a doctor, heads to the patient home, and the pieces of the position information match each other on arrival at the patient home. Thus, the doctor can download the patient information and browse it during medical treatment. After the doctor ends the medical treatment and leaves the patient home, the pieces of the position information do not match each other, and thus the patient information is deleted from the mobile information terminal 100.

Thus, leakage of the patient information caused by a terminal user's mistake while moving to the visiting destination can be prevented.

Next, a second exemplary embodiment will be described. The present exemplary embodiment is an example where downloaded patient information can be uploaded at a mobile information terminal 100. In this case, when the patient information is updated by a terminal user, such as a doctor, adding medical treatment information while treating the patient after the patient information has been downloaded to the mobile information terminal 100 at a patient home, for example. The following example is the case in which the updated patient information is automatically uploaded when the terminal user leaves the patient home.

Figure 6:
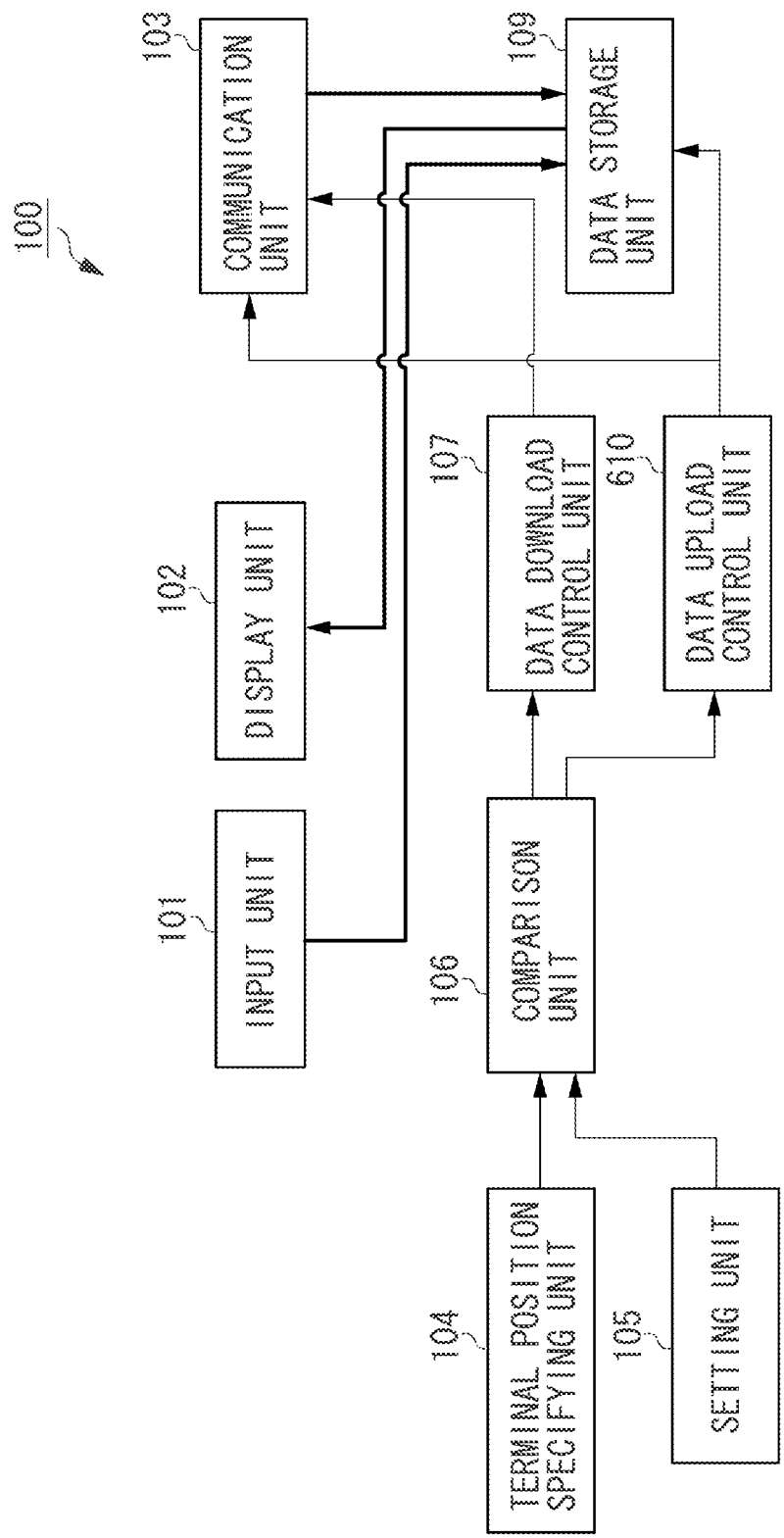
FIG. 6 is a block diagram illustrating an example of a configuration of a mobile information terminal according to a second exemplary embodiment.

FIG. 6 is a block diagram illustrating a configuration of the mobile information terminal 100 according to the second exemplary embodiment. Components similar to those of the first exemplary embodiment will be denoted by the same reference numerals, and differences of the second exemplary embodiment from the first exemplary embodiment will be mainly described.

The input unit 101 is for updating patient information, for example, by adding medical treatment information to the patient information stored in the data storage unit 109.

The communication unit 103, which has a communication function for the mobile information terminal 100 to communicate with an external device, performs communication to download and upload patient information from and to, for example, a server of a hospital.

A data upload control unit 601 controls uploading of the patient information stored in the data storage unit 109 to the server. The data upload control unit 601 determines whether to upload the patient information according to position difference information from the comparison unit 106. When uploading is necessary, the patient information in the data storage unit 109 is uploaded to the server via the communication unit 103, and then deleted from the data storage unit 109.

Figure 7:
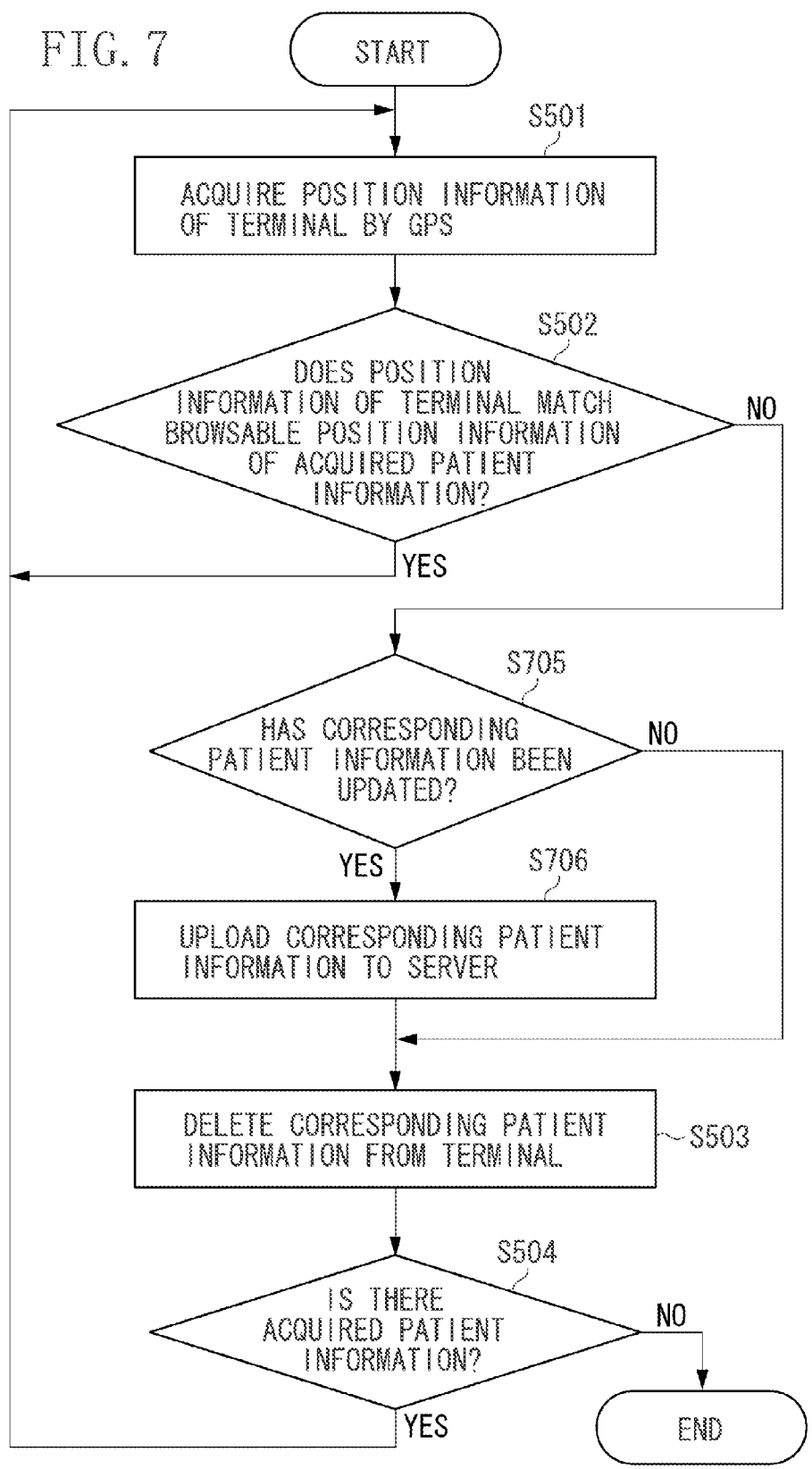
FIG. 7 is a flowchart illustrating an example of a processing procedure when the mobile information terminal according to the second exemplary embodiment deletes patient information after uploading the patient information.

FIG. 7 is a flowchart illustrating a processing procedure when the mobile information terminal 100 uploads the patient information.

Steps S501 to S504 are similar to those illustrated in FIG. 5.

If it is determined that terminal position information obtained in step S501 does not match browsable position information associated with a patient ID, of which patient information is stored in the data storage unit 109, in a position information table (No in step S502), the processing proceeds to step S705.

In step S705, the data upload control unit 601 determines whether the patient information of the patient ID having position information, which is unmatched with the terminal position information in step S502, has been updated. If not updated (NO in step S705), the processing proceeds to step S503. If updated (YES in step S705), the processing proceeds to step S706.

In step S706, the data upload control unit 610 uploads the patient information, which is determined to have been updated in step S705, to the server via the communication unit 103, and then the processing proceeds to step S503.

In step S503, the data upload control unit 610 deletes the patient information of the patient ID having position information, which is unmatched with the terminal position information in step S502, from the data storage unit 109.

In step S504, the data upload control unit 610 determines whether there is any obtained patient information in the data storage unit 109. If there is obtained patient information (YES in step S504), the processing returns to step S501. If not (No in step S504), the processing is ended.

The mobile information terminal 100, which has obtained the patient information through the processing procedure illustrated in FIG. 3, deletes the patient information through the processing procedure illustrated in FIG. 7. At the procedure, the mobile information terminal 100 uploads the patient information as necessary, and continues the processing until there is no more patient information stored in the mobile information terminal 100.

Through the series of procedures illustrated in FIGS. 3 and 7, the mobile information terminal 100 can download the patient information only at a specific position, which has been set in the position information table, associated with the patient. When the position of the mobile information terminal 100 does not match the specific position, which has been set in the position information table, associated with the patient, the patient information is uploaded if it has been updated. Then the mobile information terminal 100 deletes the patient information from the mobile information terminal 100.

When browsable position information 202 is set at a patient home as a visiting destination, a terminal user, such as a doctor, heads to the patient home, and the pieces of the position information match each other on arrival at the patient home. Thus, the doctor can download the patient information and browse it during medical treatment. After the doctor ends the medical treatment and leaves the patient home, the pieces of the position information do not match each other. Therefore, the patient information is automatically uploaded and simultaneously deleted from the mobile information terminal 100.

Thus, leakage of the patient information caused by a terminal user's mistake while moving to the visiting destination can be prevented. Simultaneously, writing-back is certainly performed for the patient information updated at the visiting destination. As a result, convenience for the terminal user can be improved.

Next, a third exemplary embodiment will be described. The present exemplary embodiment will be described using the following example in which patient information is encrypted and stored beforehand in a mobile information terminal 100. Terminal position information is compared with browsable position information, and if the pieces of position information match each other, the patient information is decrypted for browsing.

Figure 8:
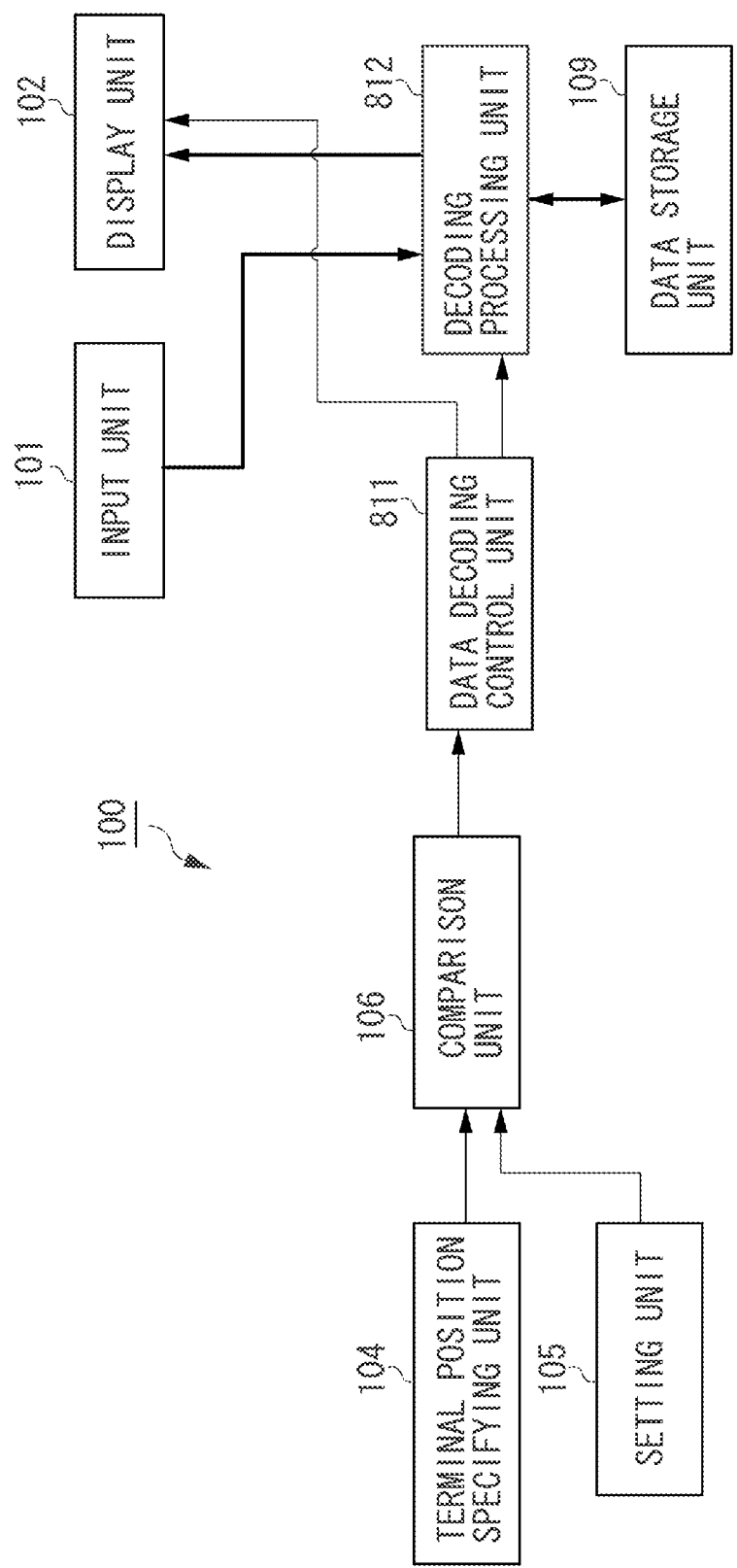
FIG. 8 is a block diagram illustrating an example of a configuration of a mobile information terminal according to a third exemplary embodiment.

FIG. 8 is a block diagram illustrating a configuration of the mobile information terminal 100 according to the third exemplary embodiment. Components similar to those of the first exemplary embodiment will be denoted by the same reference numerals, and differences of the third exemplary embodiment from the first exemplary embodiment will be mainly described.

The data storage unit 109 stores encrypted patient information. Before going out for a house visit, patient information of a patient at a visiting destination is encrypted, and is stored it in the encrypted state in the data storage unit 109.

When displaying the encrypted patient information stored in the data storage unit 109 on a display unit 102, a data decoding control unit 811 controls decoding processing for decrypting the encrypted patient information. The data decoding control unit 811 stores the decoded patient information in the data storage unit 109. The data decoding control unit 811 determines whether the patient information can be browsed according to position difference information from a comparison unit 106. In the case of a condition that browsing is permitted, the patient information is decoded via the data decoding control unit 811, and converted into browsable data to be displayed on the display unit 102. When the patient information is decoded for browsing, the data decoding control unit 811 determines whether the browsable state can be maintained according to the position difference information from the comparison unit 106. In the case of a condition that browsing is not permitted, the decoded patient information is deleted so as not to be displayed on the display unit 102.

Figure 9:
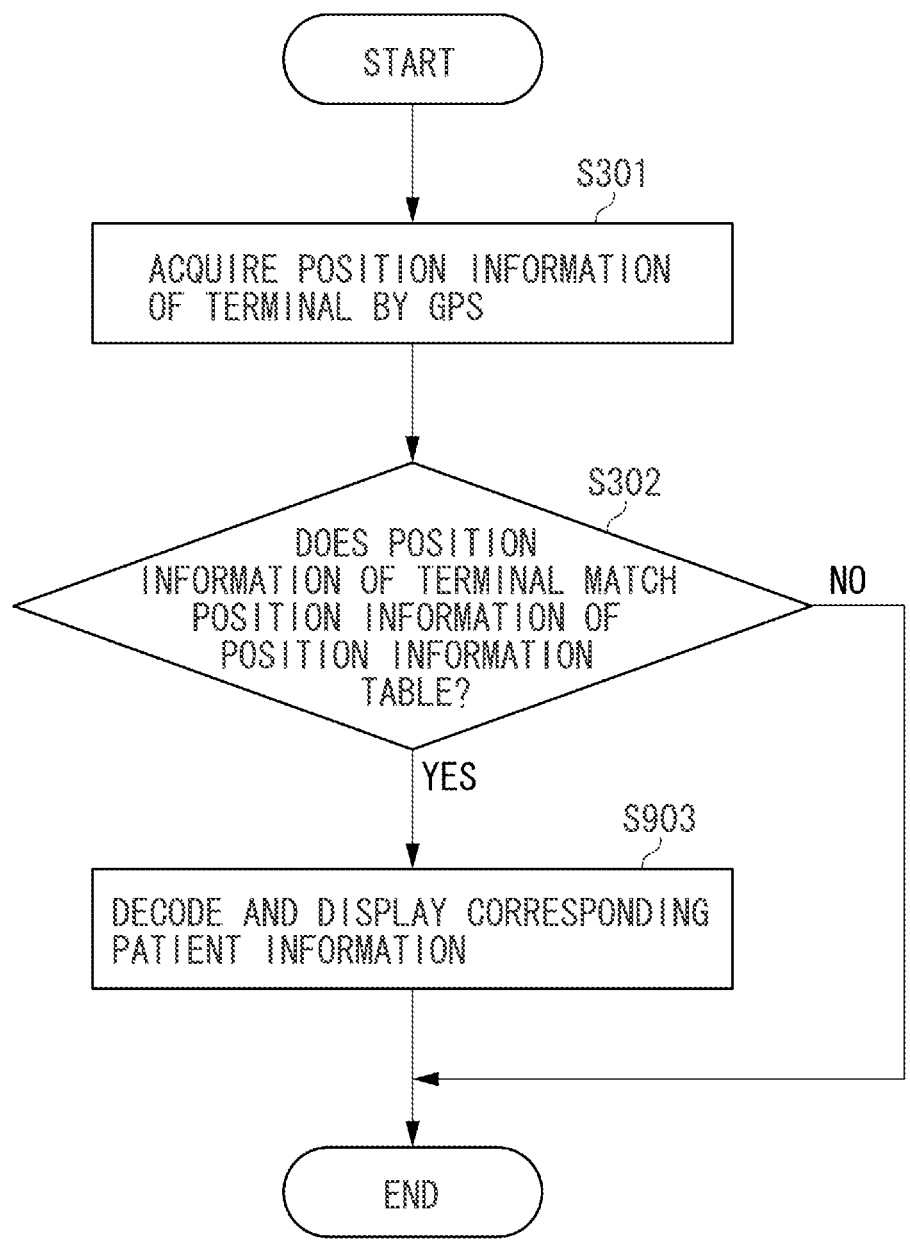
FIG. 9 is a flowchart illustrating an example of a processing procedure when the mobile information terminal according to the third exemplary embodiment decodes and displays patient information after uploading the patient information.

FIG. 9 is a flowchart illustrating a processing procedure when the mobile information terminal 100 decodes and displays patient information.

Steps S301 and S302 are similar to those having the same numerals illustrated in FIG. 3.

In step S903, the data decoding control unit 811 performs decoding processing by a decoding processing unit 812 to decrypt patient information of the patient ID having the position information, which is determined to be matched with the mobile terminal position information in step S302, and displays the decrypted patient information on the display unit 102.

Figure 10:
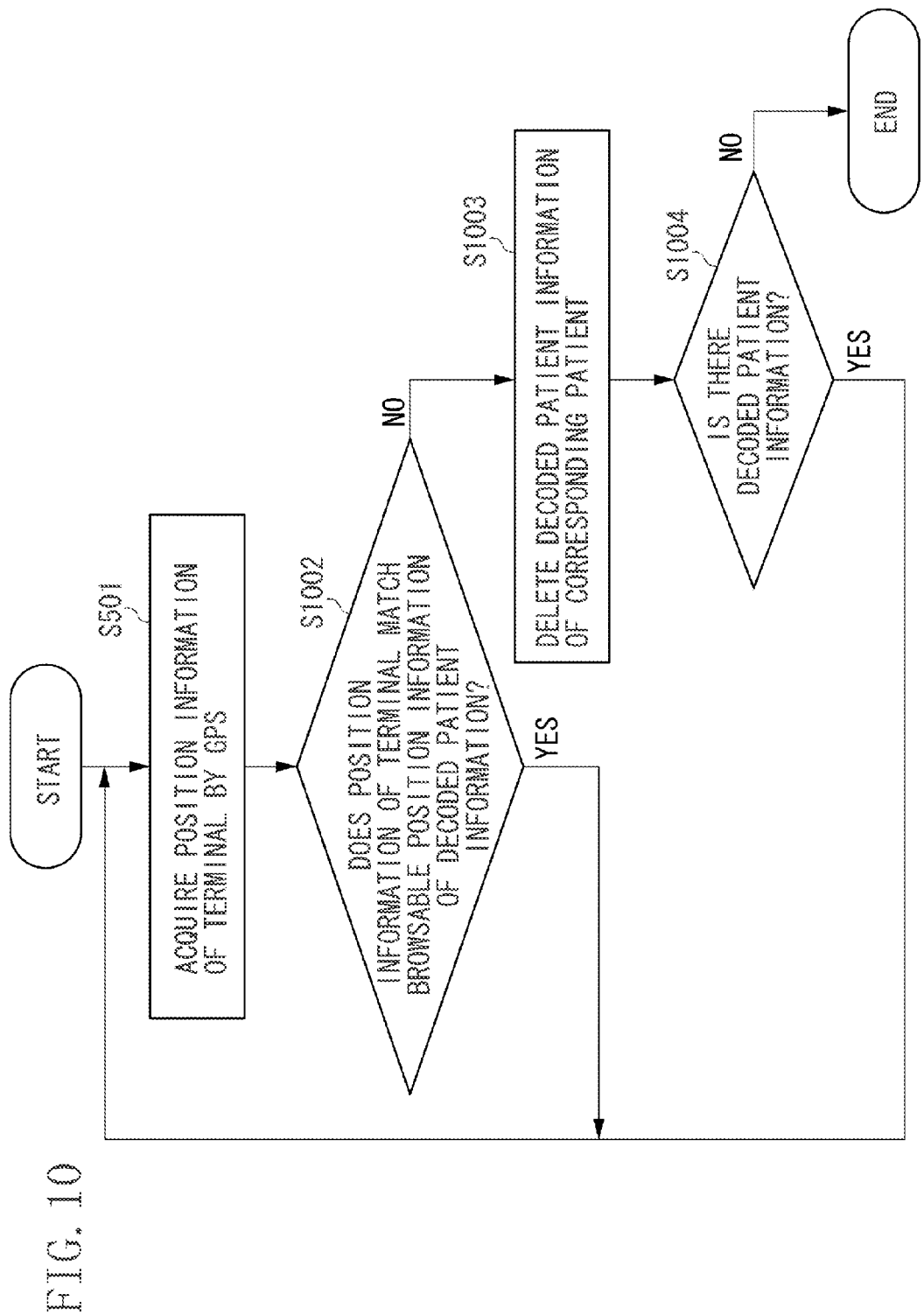
FIG. 10 is a flowchart illustrating an example of a processing procedure when the mobile information terminal according to the third exemplary embodiment deletes the decoded patient information.

FIG. 10 is a flowchart illustrating an example of a processing procedure when the mobile information terminal deletes the decoded patient information.

Step S501 is similar to that having the same numeral illustrated in FIG. 5.

In step S1002, the comparison unit 106 compares the terminal position information obtained in step S501 with the browsable position information associated with the patient ID, of which patient information stored in the data storage unit 109, in a position information table. If the pieces of position information match each other (YES in step S1002), the processing returns to step S501. If the pieces of position information do no match each other (NO in step S1002), the processing proceeds to step S1003. "The pieces of position information match each other" may be a condition that a difference in position is within a predetermined range.

In step S1003, the data decoding control unit 811 deletes only decoded patient information of the patient ID having position information, which is unmatched with the terminal position information in step S1002, from the data storage unit 109 to inhibit its displaying on the display unit 102.

In step S1004, the data decoding control unit 811 determines whether there is any pieces of the decoded patient information in the data storage unit 109. If there is the decoded patient information (YES in step S1004), the processing returns to step S501. If not (No in step S1004), the processing is ended.

The mobile information terminal 100, which has decoded the patient information to be browsable through the processing procedure illustrated in FIG. 9, deletes the decoded patient information through the processing procedure illustrated in FIG. 10, and continues the processing until there is no more decoded patient information stored in the mobile information terminal 100.

Through the series of procedures illustrated in FIGS. 9 and 10, the patient information can be browsed at the mobile information terminal 100 only at a specific position, which has been set in the position information table, associated with the patient. When the position of the mobile information terminal 100 does not match the specific position, which has been set in the position information table, associated with the patient, the patient information cannot be browsed any more at the mobile information terminal 100.

Before going out for a house visit, in a place such as a hospital where security is assured, the browsable position information 202 for a patient of a visiting destination is set at a patient home as the visiting destination, and the patient information is encrypted to be stored in the terminal 100. A terminal user, such as a doctor, heads to the patient home, and the pieces of the position information match each other on arrival at the patient home. Thus, the patient information is decoded and the doctor can browse it during medical treatment. After the doctor ends the medical treatment and leaves the patient home, the pieces of position information do not match each other. Therefore, the patient information cannot be browsed at the mobile information terminal 100.

As described above, leakage of the patient information caused by a terminal user's mistake while moving to the visiting destination can be prevented.

Next, a fourth exemplary embodiment will be described. The present exemplary embodiment will be described using an example in which, in addition to the setting of browsable position information, medical treatment type information is set for selecting information among pieces of patient information, which is necessary for medical treatment at a visiting destination. With such an arrangement, a risk of patient information leakage is reduced by limiting information to be downloaded at the visiting destination. In addition, convenience during browsing of patient information at the visiting destination is improved by permitting a change of a medical treatment type only at a registered browsable position.

Figure 11:
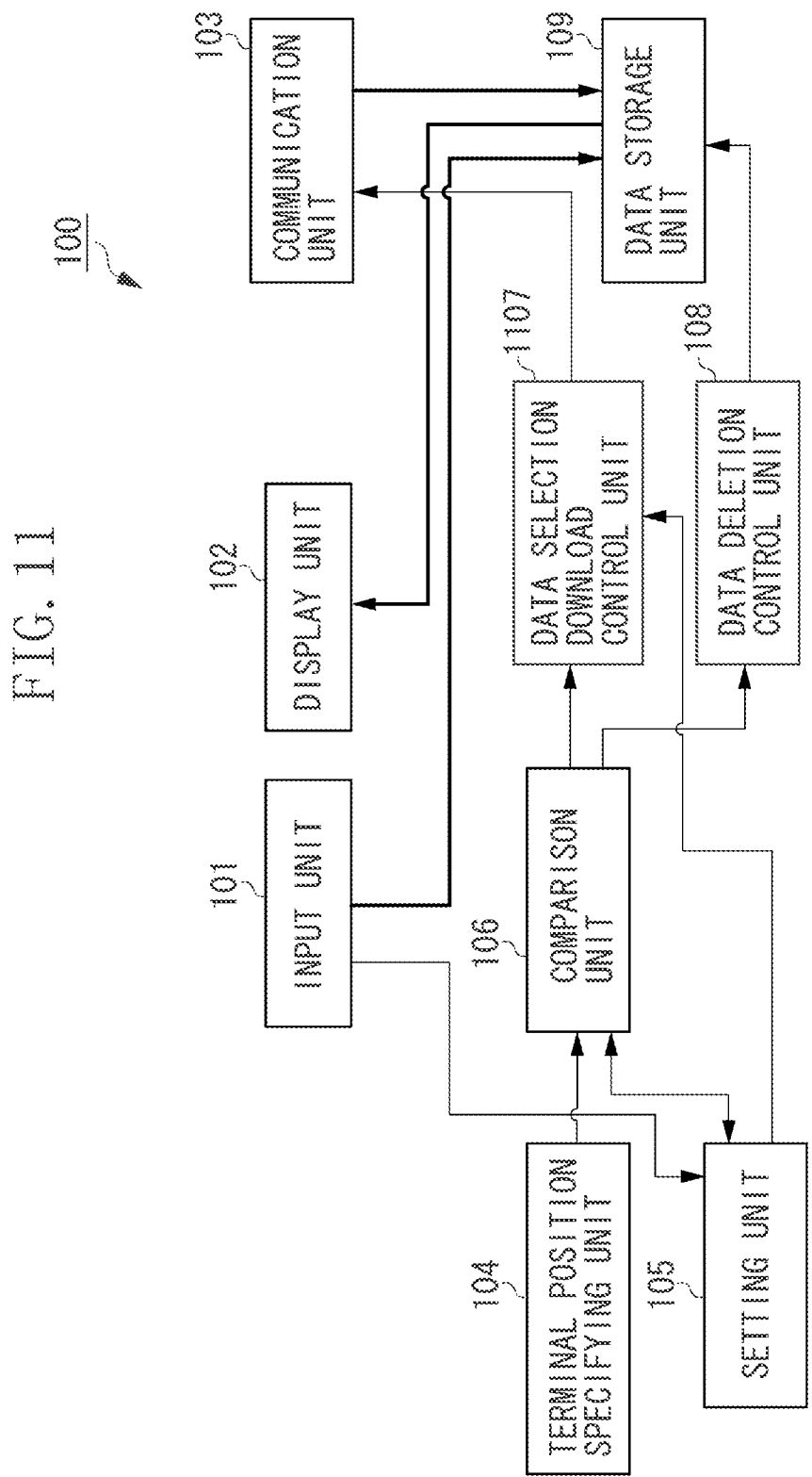
FIG. 11 is a block diagram illustrating an example of a configuration of a mobile information terminal according to a fourth exemplary embodiment.

FIG. 11 is a block diagram illustrating a configuration of a mobile information terminal 100 according to the fourth exemplary embodiment. Components similar to those of the first exemplary embodiment will be denoted by the same reference numerals, and differences of the fourth exemplary embodiment from the first exemplary embodiment will be mainly described.

An instruction can be issued by the input unit 101 for a change of a medical treatment type described below.

A setting unit 1105 sets browsable position information and medical treatment type information for each patient information (in other words, for each patient). To limit positions for browsing patient information for a patient to be visited, the setting unit 1105 sets the browsable position information in association with a patient ID of the patient. Examples as a position for browsing the patient information include a patient home, a hospital, and a doctor's home. The medical treatment type information is for selecting information among pieces of patient information, which is necessary for medical treatment at a visiting destination. The browsable position information and the medical treatment type information are set by the setting unit 1105, and stored in a position/medical treatment type information table described below, which is stored by the setting unit 1105.

A data selection download control unit 1107 controls downloading of patent information to the mobile information terminal 100. The data selection download control unit 1107 determines whether the patient information can be downloaded according to position difference information by a comparison unit 106. When the patent information can be downloaded, the data selection download control unit 1107 downloads the patent information via a communication unit 103 to store it in a data storage unit 109. When downloading the patient information, the data selection download control unit 1107 selectively downloads necessary information from the pieces of patient information based on medical treatment type information stored in the position/medical treatment type information table.

FIG. 12 illustrates an example of the position/medical treatment type information table. The position/medical treatment type information table stores a patient ID 201, browsable position information 202 set by the setting unit 1105, and medical treatment type information 1203 set by the setting unit 1105.

The medical treatment type information 1203 is setting information for selectively downloading necessary information from pieces of patient information of a patient identified by the patient ID 201. As the medical treatment type information, for example, two kinds of type information, i.e., "continuous" and "new", can be set. The "continuous" is a type intended to perform periodical treatment of disease continuous from a last visit, and only patient information related to a current disease name of the patient is downloaded. For example, in the case of a patient currently having diabetes, only patient information related to the disease is downloaded, while information about previously treated tuberculosis is not downloaded. The "new" is a type intended to visit a patient's house when a new disease condition appears. In such a case, past disease history is also needed for diagnosis, and thus all pieces of information about the patient are downloaded. For example, as patient information, disease names from the past to the present as disease history information is recorded in the server. The data selection download control unit 1107 can have a current disease name by reference of the latest disease name included in the disease history information.

A processing procedure for obtaining the patient information by the mobile information terminal 100 is similar to that illustrated in FIGS. 3 and 4. However, an information amount to be downloaded is different. Specifically, when patient information of a patient ID having matched location information is obtained, only necessary patient information is downloaded based on the medical treatment type information of the patient.

Next, a case in which changing of a medical treatment type is necessary at a visiting destination is described below. Before visiting a patient's house, a medical treatment type may not be appropriately determined. Also, a diagnosis may be made as new disease only by visiting. Accordingly, during treatment of the patient at the visiting destination, downloading of all the pieces of patient information by changing medical treatment types is enabled. Also in this case, a risk of patient information leakage is reduced by performing control to enable a terminal user to change a medical treatment type only when the terminal 100 is present at a designated position.

Figure 13:
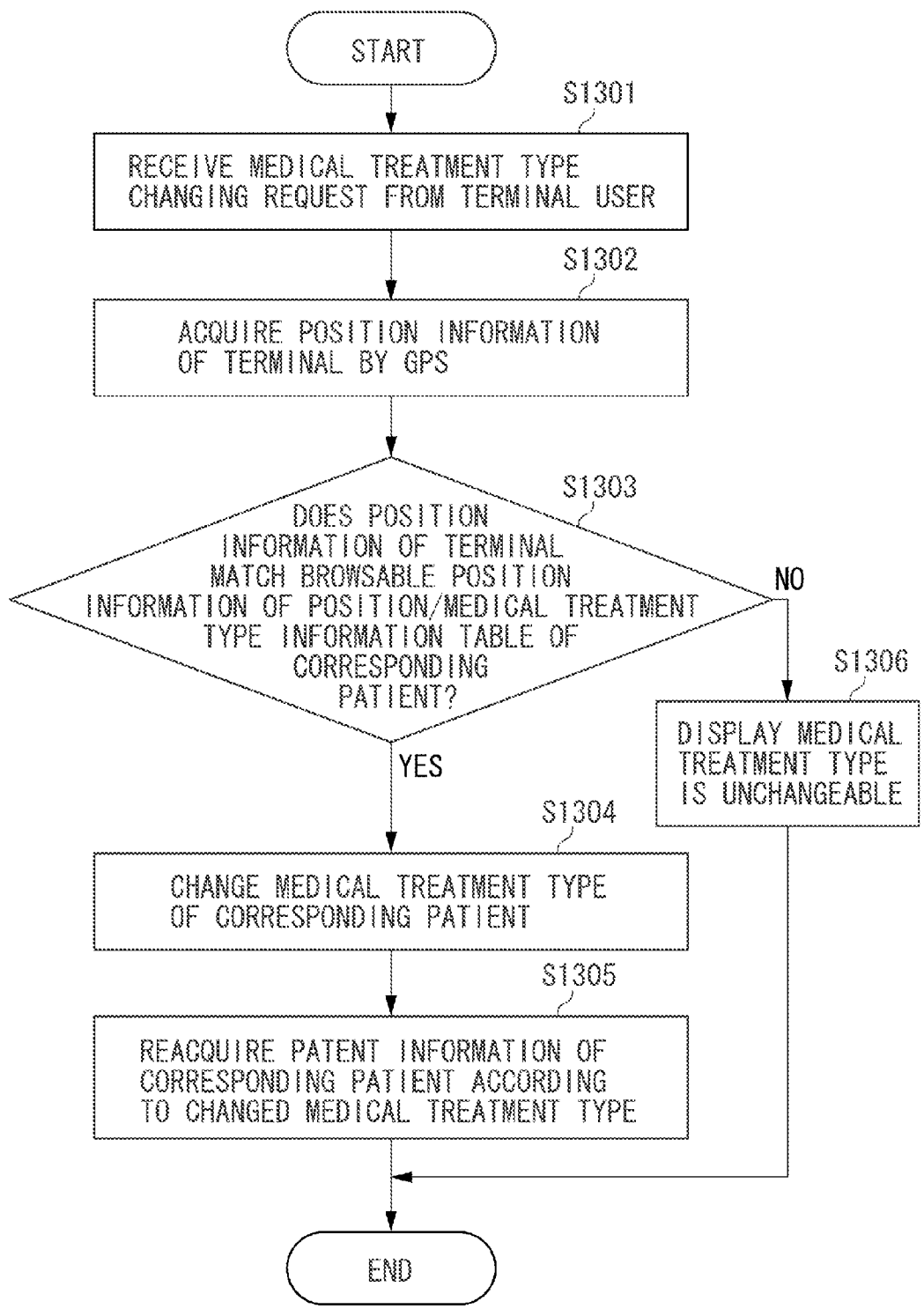
FIG. 13 is a flowchart illustrating an example of a processing procedure when the mobile information terminal according to the fourth exemplary embodiment changes medical treatment type information.

FIG. 13 is a flowchart illustrating a processing procedure when the mobile information terminal 100 changes medical treatment type information.

In step S1301, a changing request of medical treatment type information is received from a terminal user via the input unit 101.

In step S1302, the terminal position specifying unit 104 obtains current terminal position information by using a GPS function.

In step S1303, the comparison unit 106 compares the terminal position information obtained in step S1302 with the browsable position information 202 stored in the position/medical treatment type information table. If the pieces of the position information do not match each other (No in step S1303), the processing proceeds to step S1306. If the pieces of the position information match each other (YES in step S1303), the processing proceeds to step S1304. "the pieces of the position information match each other" can be a condition that a difference in position is within a predetermined range.

In step S1304, the setting unit 1105 changes a medical treatment type of patient ID having position information, which is matched with the terminal position information in step S1303, according to an input from the terminal user via the input unit 101.

In step S1305, the data selection download control unit 1107 downloads, based on the medical treatment type information changed in step S1304, patient information of the patient ID having position information, which is matched with the terminal position information in step S1303, via the communication unit 103 to store it in the data storage unit 109.

In step S1306, the setting unit 1105 displays that the medical treatment type is unchangeable to the terminal user, and the processing is ended.

Through the processing procedure illustrated in FIG. 13, the mobile information terminal 100 can change the medical treatment type information only at a specific position, which is set in the position/medical treatment type information table, associated with the patient. Thus, a risk of patient information leakage can be reduced while maintaining convenience that additional downloading of patient information can be performed according to a patient's condition at the visiting destination.

As described above, by enabling changing of the medical treatment type information at the visiting destination while limiting information to be downloaded at the visiting destination based on the medical treatment type information, reduction of a risk of patient information leakage and improvement of convenience during browsing of patient information can be simultaneously achieved.

Additional embodiments can also be realized by a computer of a system or apparatus that reads out and executes computer executable instructions recorded on a storage medium (e.g., computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2013-062499 filed Mar. 25, 2013, which is hereby incorporated by reference herein in its entirety.

What is claimed is:

1. A mobile information terminal comprising:
   at least one processor; and
   as least one memory storing position information set for each piece of personal information for browsing the personal information, and computer-executable instructions to be executed by the at least one processor to perform a method comprising:
   specifying a position of the mobile information terminal;
   communicating with an external device that manages the personal information;
   downloading the personal information from the external device according to a result of comparing the specified position information with the stored position information; and
   deleting the downloaded personal information from the mobile information terminal according to a result of comparing the specified position information with the stored position information.

2. The mobile information terminal according to claim 1, wherein:
   the downloaded personal information can be updated at the mobile information terminal; and
   the deleting includes uploading the personal information that has been downloaded and updated according to the result of comparing the specified position information with the stored position information, and then deleting the personal information from the mobile information terminal.

3. The mobile information terminal according to claim 1, wherein the downloading includes downloading the personal information in a case where the specified position information matches the stored position information, and the deleting includes deleting the downloaded personal information in a case where the specified position information does not match the stored position information.

4. The mobile information terminal according to claim 1, wherein the method further comprises:
   receiving an input for updating the downloaded personal information,
   wherein, in a case where the input has been received, the deleting includes deleting the downloaded personal information from the mobile information terminal after the downloaded personal information which is updated according to the received input has been uploaded to the external device.

5. The mobile information terminal according to claim 1, wherein the deleting includes deleting the downloaded personal information in a case where the specified position information does not match the stored position information.

6. The mobile information terminal according to claim 1, wherein the downloading includes downloading the personal information in a case where the specified position information matches the stored position information.

7. The mobile information terminal according to claim 1, wherein the downloading includes, when downloading the personal information from the external device, downloading the personal information based on type information.

8. The mobile information terminal according to claim 7, wherein the type information is medical treatment type information and indicates whether medical treatment is new or continuous.

9. A mobile information terminal comprising:
   at least one processor; and
   as least one memory storing position information set for each piece of personal information for browsing the personal information, and computer-executable instructions to be executed by the at least one processor to perform a method comprising:
   specifying a position of the mobile information terminal;
   communicating with an external device that manages the personal information; and
   downloading the personal information from the external device according to a result of comparing the specified position information with the stored position information,
   wherein:
   the at least one memory stores the position information set for each piece of personal information in association with type information; and
   the downloading includes, when downloading the personal information from the external device, downloading the personal information based on the type information.

10. The mobile information terminal according to claim 9, wherein the type information changes at the mobile information terminal according to the result of comparing the specified position information with the stored position information.

11. The mobile information terminal according to claim 9, wherein the type information is medical treatment type information and indicates whether medical treatment is new or continuous.

\* \* \* \* \*